US012629129B2

(12) United States Patent
Chen et al.

(10) Patent No.: US 12,629,129 B2
(45) Date of Patent: May 19, 2026

(54) ARRAY MEASURING METHOD AND INTERPRETATION DEVICE FOR ULTRASONIC DETECTION OF MIDDLE EAR EFFUSION

(71) Applicants:CHANG GUNG MEMORIAL HOSPITAL, LINKOU, Taoyuan City (TW); CHANG GUNG UNIVERSITY, Taoyuan City (TW)

(72) Inventors: Chin-Kuo Chen, Taoyuan City (TW); Po-Hsiang Tsui, Taoyuan City (TW)

(73) Assignees: CHANG GUNG MEMORIAL HOSPITAL, LINKOU, Taoyuan City (TW); CHANG GUNG UNIVERSITY, Taoyuan City (TW)

( * ) Notice: Subject to any disclaimer, the term of this patent is extended or adjusted under 35 U.S.C. 154(b) by 76 days.

(21) Appl. No.: 18/836,849

(22) PCT Filed: Feb. 10, 2022

(86) PCT No.: PCT/CN2022/075810
§ 371 (c)(1),
(2) Date: Aug. 8, 2024

(87) PCT Pub. No.: WO2023/150960
PCT Pub. Date: Aug. 17, 2023

(65) Prior Publication Data
US 2025/0040908 A1 Feb. 6, 2025

(51) Int. Cl.
*A61B 8/08* (2006.01)
*A61B 8/00* (2006.01)

(52) U.S. Cl.
CPC ............ *A61B 8/085* (2013.01); *A61B 8/4494* (2013.01); *A61B 8/5207* (2013.01)

(58) Field of Classification Search
CPC ......... A61B 8/00; A61B 8/085; A61B 8/4494; A61B 8/5207
See application file for complete search history.

(56) References Cited

U.S. PATENT DOCUMENTS 7,131,946 B2    11/2006   Lewandowski
2004/0167404 A1    8/2004   Bessler
(Continued)

FOREIGN PATENT DOCUMENTS

KR      20090128613 A    12/2009
TW      200718399 A    5/2007
(Continued)

OTHER PUBLICATIONS

Won et al. "Assessing the Effect of Middle Ear Effusions on Wideband Acoustic Immittance Using Optical Coherence Tomography", Jul./Aug. 2000 (Year: 2000).*
(Continued)

*Primary Examiner* — Brooke Lyn Klein
(74) *Attorney, Agent, or Firm* — WPAT, PC

(57) ABSTRACT

The present disclosure provides an array measuring method and interpretation device for ultrasonic detection of middle ear effusion, including an ultrasonic probe, an ultrasonic receiver, an analog-to-digital converter, and an analysis unit. The surface of the mastoid is divided into a plurality of measurement areas, and when ultrasonic is used for non-invasive detection of middle ear effusion, linear discriminant analysis is used for pre-training to find the best detection position and weighting parameters thereof to obtain the accurate evaluation value.

11 Claims, 5 Drawing Sheets

(56)     References Cited

U.S. PATENT DOCUMENTS

| 2010/0069752 A1 | 3/2010 | Lewandowski |
| 2018/0182101 A1* | 6/2018 | Petersen ................... G06T 7/60 |

FOREIGN PATENT DOCUMENTS

| TW | 201507701 A | 3/2015 |
| TW | 201641936 A | 12/2016 |

OTHER PUBLICATIONS

Chen et al. "Ultrasound characterization of the mastoid for detecting middle ear effusion: A preliminary clinical validation", Feb. 9, 2016 (Year: 2016).*

Translated copy of Foreign Chen (TW201507701 A) (Year: 2015).*

O. Clade et al., "Development and Evaluation of a 20MHz Array for Ultrasonic Detection of Middle Ear Effusion", 2006 IEEE Ultrasonics Symposium, Oct. 6, 2006(Oct. 6, 2006), pp. 2357-2360, IEEE.

Chen, Chinkuo et al., "Using 1 MHz pulse-echo ultrasound externally applied to detect mastoid effusion: cadaver experiments", Ultrasonics, vol. 52, No. 5, Jul. 31, 2012 (Jul. 31, 2012), ISSN: 0041-624X, pp. 663-667, Elsevier.

* cited by examiner (1-Specificity)

(1-Specificity)

ARRAY MEASURING METHOD AND INTERPRETATION DEVICE FOR ULTRASONIC DETECTION OF MIDDLE EAR EFFUSION

BACKGROUND OF THE INVENTION

1. Field of the Invention

The present invention relates to an array measuring method and interpretation device for ultrasonic detection of middle ear effusion, especially an array measuring method and interpretation device for ultrasonic detection of middle ear effusion based on a single-element ultrasonic probe and combined with probability density function parameters of multiple array measurement areas.

2. The Prior Art

Otitis media is a common disease in children. It is the most common disease for which antibiotics are used. It is also one of the main reasons why children need surgery. The probability of otitis media complicated by middle ear effusion is high and is not noticed. Moreover, if middle ear effusion is not treated, it would lead to many complications and is a potential killer of hearing loss. Therefore, diagnosing middle ear effusion has important clinical value.

Clinically, otoscopy is the most basic and direct way to examine middle ear effusion. It mainly examines the appearance of the eardrum or uses air blowing to observe the vibration of the eardrum to determine whether there is fluid in the middle ear. However, diagnosis is highly dependent on the doctor's experience and can easily fall into subjective judgment. Tympanography is another method commonly used to evaluate middle ear effusion. It is similar to blowing air into the eardrum and measuring the movement of the eardrum in response to changes in pressure. However, patients need to cooperate with the ear canal sealing and pressurization test. This is often because children are afraid or crying and have difficulty communicating, which affects the tightness of the earplugs and the ear canal, and the test time is also difficult to control.

Medical imaging systems such as computer tomography and nuclear magnetic resonance imaging are currently the standard methods for detecting middle ear effusion. However, computer tomography has the concern of producing radiation, and the above two methods require a long measurement time, and the measurement environment is relatively closed. For patients with otitis media, especially children, it is easy to have a resistance reaction. In addition, computer tomography and nuclear magnetic resonance imaging are also limited by the size of the device, as well as the time and place of use. Compared with imaging systems in related technologies, ultrasound provides a non-invasive and non-radiative way, applicable to any place and at any time, and can be used to evaluate the interpretation of middle ear effusion before and after surgery.

Currently, U.S. patent publication Nos. U.S. Pat. No. 7,131,946 and US20100069752 have disclosed the use of ultrasonic probes inserted into the ear canal to detect middle ear effusion. However, the measurement method is still invasive and is particularly unsuitable for detecting middle ear effusion in children. Taiwan of the People's Republic of China patent No. 1549657 discloses the use of ultrasonic probes attached to the position behind the user's ears corresponding to the mastoid process to serve as a sound window for non-invasive measurement, and based on the statistical characteristics of the ultrasonic echo signal, the subject's middle ear effusion status is determined. Although this technology overcomes the previous dilemma that the ultrasonic probe must be inserted into the ear canal to assess middle ear effusion, due to the large mastoid area, if the measurement position cannot be accurately controlled, the detection results would be inaccurate due to the uncertainty of the measurement position.

In summary, compared with imaging systems in related technologies, it is indeed necessary to develop a method and interpretation device that is non-invasive, has no radiation concerns, can be used anywhere and at any time, and can accurately assess the degree and condition of middle ear effusion.

SUMMARY OF THE INVENTION

A primary objective of the present invention is to provide an array measuring and interpretation device for ultrasonic detection of middle ear effusion, comprising: an ultrasonic probe, attached to a mastoid surface behind a user's ear and sending an ultrasound wave, wherein the mastoid surface is divided into a plurality of array measurement areas, and an ultrasonic echo signal is generated in each array measurement area according to the user's middle ear effusion condition; an ultrasonic receiver, connected to the ultrasonic probe and receiving the ultrasonic echo signal of each array measurement area; an analog-to-digital converter, connected to the ultrasonic receiver and converting the ultrasonic echo signal into a digital signal; and an analysis unit, connected to the analog-to-digital converter, wherein the analysis unit calculates a probability density function parameter of each array measurement area based on the digital signal, and uses a pre-trained model to find an importance weight corresponding to the probability density function parameter of each array measurement area, wherein the probability density function parameter of each array measurement area is multiplied by the importance weight and then summed to generate a weighted probability density function parameter for quantifying degree of middle ear effusion of the user, thereby determining the user's middle ear disease condition.

According to an embodiment of the present invention, the ultrasonic probe is a low frequency delay probe.

According to an embodiment of the present invention, the analysis unit is a personal computer.

Another objective of the present invention is to provide an array measuring and interpretation method for ultrasonic detection of middle ear effusion, comprising the following steps: attaching an ultrasonic probe to a mastoid surface behind a user's ear and sending an ultrasound wave, dividing the mastoid surface into a plurality of array measurement areas, generating an ultrasonic echo signal in each array measurement area according to the user's middle ear effusion condition, and receiving the ultrasonic echo signal of each array measurement area by using an ultrasonic receiver; and converting the ultrasonic echo signal into a digital signal by using an analog-to-digital converter; wherein an analysis unit calculates a probability density function parameter of each array measurement area based on the digital signal, and uses a pre-trained model to find an importance weight corresponding to the probability density function parameter of each array measurement area, wherein the probability density function parameter of each array measurement area is multiplied by the importance weight and then summed to generate a weighted probability density function parameter for quantifying degree of middle ear effusion of the user, thereby determining the user's middle ear disease condition.

According to an embodiment of the present invention, the importance weight of the probability density function parameter corresponding to each array measurement area is found using linear discriminant analysis and the pre-trained model.

According to an embodiment of the present invention, the mastoid surface is divided into 12 array measurement areas.

According to an embodiment of the present invention, the array measuring and interpretation method for ultrasonic detection of middle ear effusion improves accuracy of determining severity of middle ear effusion of the user.

According to an embodiment of the present invention, the array measuring and interpretation method for ultrasonic detection of middle ear effusion improves accuracy of determination of types of the user's middle ear effusion.

According to another embodiment of the present invention, the middle ear disease includes various types of otitis media, middle ear effusion, mastoid effusion, mastoiditis, and tracking before and after ear tube implantation.

Therefore, the array measuring method and interpretation device for ultrasonic detection of middle ear effusion of the present invention uses a single-element ultrasonic probe to use the mastoid surface behind the subject's ear as the sound window and send ultrasonic signals, and then receives and analyzes the ultrasonic echo signal returned according to the condition of middle ear effusion of the subject to perform non-invasive measurements. Since the area at the mastoid is large, and there is no relevant prior art to disclose the detection position that can reflect the best measurement results, if the measurement position cannot be accurately controlled, the results would be inaccurate due to the uncertainty of the measurement position.

Accordingly, in the present invention, in order to optimize the calculation and analysis methods of the overall information and integrate it into the original operating interface, achieving easy operation and rapid classification of the condition and nature of middle ear effusion, improving the accuracy and predictability of ultrasonic-based non-invasive measurement methods and their devices, the subject's mastoid surface is further divided into a plurality of array measurement areas, and the ultrasonic echo signals of each array measurement area are obtained respectively. After calculating a probability density function parameter of each array measurement area, the data analysis software in the analysis unit is combined with linear discriminant analysis based on machine learning for pre-training to find out the importance weight of each separated measurement area in determining the condition of middle ear effusion. After weighting the probability density function parameters of each measurement area, compared with using a single parameter, the obtained new parameters can not only maintain a good ability to determine whether a patient has middle ear effusion, but can also be used to determine the severity of the patient's middle ear effusion. It can also effectively improve the ability to determine the nature (i.e., serous or mucinous) of middle ear effusion in patients.

In summary, the array measuring method and interpretation device for ultrasonic detection of middle ear effusion of the present invention can improve the existing shortcomings of the prior art. It has the advantages of non-invasiveness, no radiation, and can be used anywhere and at any time. It is especially suitable for measuring middle ear effusion in children. And if the present invention is used to repeatedly measure the user's middle ear effusion before and after surgery, it can be used to evaluate whether the middle ear effusion has been cleared before and after surgery. Most importantly, the data analysis method of the present invention can also reduce the uncertainty caused by subjective judgment, making the diagnosis of middle ear effusion faster, more convenient to operate, and the test results more accurate.

Embodiments of the present disclosure would be further described below. The examples listed below are used to illustrate the present disclosure and are not intended to limit the scope of the present disclosure. Anyone skilled in the art may make slight changes and modifications without departing from the spirit and scope of the present disclosure. Therefore, the scope of the present disclosure shall be determined by the scope of the appended claims.

REFERENCE SIGNS

1: Array measuring and interpretation device for ultrasonic detection of middle ear effusion
11: Ultrasonic probe
12: Ultrasonic receiver
13: Analog-to-digital converter
14: Analysis unit

DETAILED DESCRIPTION OF THE
PREFERRED EMBODIMENT

According to the present invention, the operating procedures and parameter conditions for ultrasonic detection and reception, including ultrasonic probes and ultrasonic receivers, fall within the professionalism and routine technical scope of those skilled in the art.

According to the present invention, the operating procedures and parameter conditions of the analog-to-digital converter fall within the professionalism and routine technical scope of those skilled in the art.

Figure 1A:
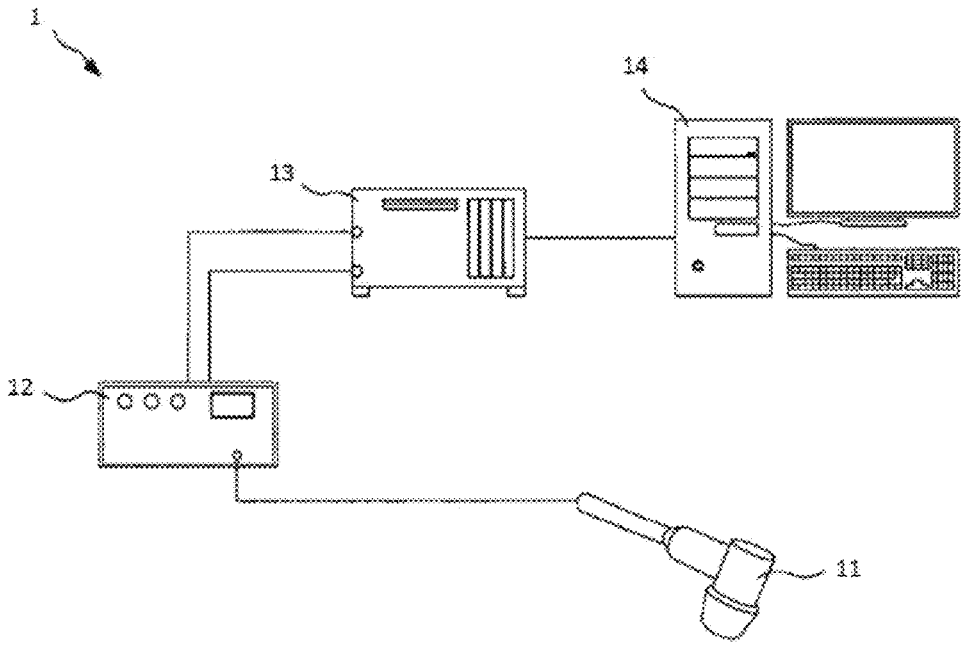
FIG. 1A is a schematic diagram of the components of the array measuring and interpretation device for ultrasonic detection of middle ear effusion according to the present invention.

Referring to FIG. 1A, which is a schematic diagram of the components of the array measuring and interpretation device for ultrasonic detection of middle ear effusion 1 according to the present invention. The array measuring and interpretation device for ultrasonic detection of middle ear effusion 1 comprises: an ultrasonic probe 11, an ultrasonic receiver 12, an analog-to-digital converter 13, and an analysis unit 14; wherein the ultrasonic probe 11 is connected to the ultrasonic receiver 12, the ultrasonic receiver 12 is connected to the analog-to-digital converter 13, and the analog-to-digital converter 13 is connected to the analysis unit 14.

Figure 1B:
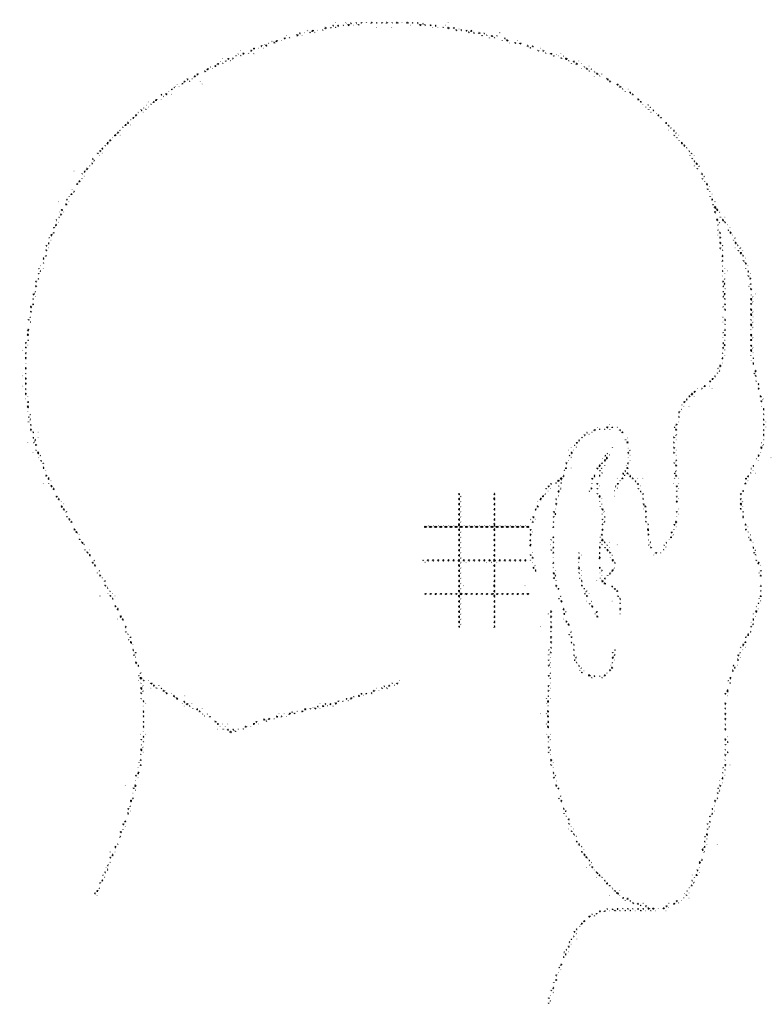
FIG. 1B is a schematic diagram of defining the user's mastoid surface into a plurality of array measurement areas.

The method of using the array measuring and interpretation device for ultrasonic detection of middle ear effusion 1 of the present invention is as follows: First, the ultrasonic probe 11 is attached to a mastoid surface behind a user's ear to send an ultrasound wave to the mastoid surface as the sound window. According to the user's middle ear effusion condition, corresponding ultrasonic echo signals are generated for non-invasive measurement. Due to the large mastoid area, it is easy to distort the results due to unstable measurement positions. Therefore, in order to improve the accuracy of signal measurement and interpretation, in the array measuring and interpretation device for ultrasonic detection of middle ear effusion of the present invention, the user's mastoid surface is first defined into a plurality of array measurement areas. Considering the size of the ultrasonic probe 11 and the size of the user's mastoid, those skilled in the art can adjust the number of array measurement areas. As shown in FIG. 1B, it is best to define twelve array measurement areas, and generate an ultrasonic echo signal for each array measurement area. Subsequently, the ultrasonic receiver 12 is used to receive all the ultrasonic echo signals, and the analog-to-digital converter 13 is used to convert the ultrasonic echo signals into a corresponding digital signal. The digital signals of each array measurement area are then sent to the analysis unit 14 for further analysis and calculation of the digital signals.

In the analysis unit 14 of the array measuring and interpretation device for ultrasonic detection of middle ear effusion 1 according to the present invention, a probability density function parameter (or called statistical dynamic differences of different orders) of each array measurement area is calculated based on the digital signals. The analysis unit 14 would analyze the data based on the digital signals of each array measurement area and their probability density functions. Pre-training is performed using machine learning-based linear discriminant analysis (LDA) (or Fisher Linear Discriminant) to find out the importance weights corresponding to the probability density function parameters (statistical dynamic differences of different orders) of each array measurement area. The weighted probability density function parameters can be obtained by multiplying the probability density function parameters of each array measurement area by the corresponding importance weights and then summing them all up. The probability density function parameters of each array measurement area are quantified through the Nakagami parameters. Therefore, when the value of the probability density function parameter is higher, it means that the user's condition is closer to the middle ear effusion to be detected (including whether there is middle ear effusion, the severity of middle ear effusion, and the nature of middle ear effusion, which would be described in detail later). After combining the importance weights, the weighted probability density function parameters also follow this judgment standard. Therefore, the weighted probability density function parameters can be used to accurately quantify the user's middle ear effusion s, and the user's middle ear disease condition can be determined accordingly.

In a preferred embodiment of the present invention, the analysis unit 14 is a personal computer. According to the present invention, the analysis unit 14 can be used with commonly available data analysis software, such as MATLAB, and provides the function of calculating numerical values such as probability density functions and importance weights.

In a preferred embodiment of the present invention, the ultrasonic probe 11 is a low frequency delay probe. Therefore, the measurement signal and the excitation pulse can be separated, thereby increasing the accuracy of the measurement signal and probability density function analysis.

Subsequently, in order to test whether the array measuring method and interpretation device for ultrasonic detection of middle ear effusion of the present invention can effectively improve the accuracy of measuring and interpreting middle ear effusion, the following three experimental group tests were conducted. (1) Whether there is middle ear effusion: The array measuring method and interpretation device for ultrasonic detection of middle ear effusion of the present invention was used to detect middle ear effusion in normal people (i.e., those without middle ear effusion), patients with middle ear effusion, and patients three months after ear tube surgery (also patients with middle ear effusion), respectively; (2) The severity of middle ear effusion: The array measuring method and interpretation device for ultrasonic detection of middle ear effusion of the present invention was used in patients with mild to moderate middle ear effusion and patients with severe middle ear effusion, respectively; and (3) The nature of middle ear effusion: The array measuring method and interpretation device for ultrasonic detection of middle ear effusion of the present invention was used in patients with serous middle ear effusion and mucinous middle ear effusion respectively. There would be three different detection purposes for the array measuring method and interpretation device for ultrasonic detection of middle ear effusion of the present invention based on whether there is middle ear effusion, the severity of middle ear effusion, and the nature of middle ear effusion. The digital signals and probability density functions of each array measurement area corresponding to the three are pre-trained using linear discriminant analysis based on machine learning to find out the importance weights corresponding to the probability density function parameters of each corresponding array measurement area among these three different detection purposes, followed by calculating the respective weighted probability density function parameters.

In addition, among the three experimental groups, the control group does not divide the surface of the mastoid into a plurality of array measurement areas, and tests the same group of people. That is, only a single probability density function parameter is used to measure and interpret the condition of middle ear effusion.

After obtaining the test results, a statistical software (such as sigmaplot) is used to plot a receiver operating characteristic curve (ROC, hereafter referred to as the ROC curve) for each experimental group for analysis. The area under the curve of ROC (AUROC) of each experimental group and the control group is compared to evaluate the accuracy of the array measuring method and interpretation device for ultrasonic detection of middle ear effusion of the present invention. The ROC curve is often used to analyze the accuracy of a detection method. It is a binary analysis model, that is, the output results are only two categories of models. For example, the experimental group (1) has middle ear effusion or no middle ear effusion, the experimental group (2) has mild, moderate or severe middle ear effusion, and the experimental group (3) has serous or mucinous middle ear effusion. A threshold is set to distinguish between the two result categories. Subsequently, the weighted probability density function parameter of each experimental group or the single probability density function parameter of each control group is brought in to determine the respective true first category, pseudo first category, true second category, and pseudo second category. The ROC curve is plotted, and the closer the area under the curve of ROC (AUROC) is to 1, the higher the accuracy of the detection method brought into the ROC curve for analysis. In the embodiment of the present invention, the following thresholds are respectively set for three different detection purposes: whether there is middle ear effusion, the severity of middle ear effusion, and the nature of middle ear effusion. >7.58 is considered to have middle ear effusion; <0.60 is considered to be severe middle ear effusion; and <−0.84 is considered to be mucinous middle ear effusion.

Figures 2A, 2B:
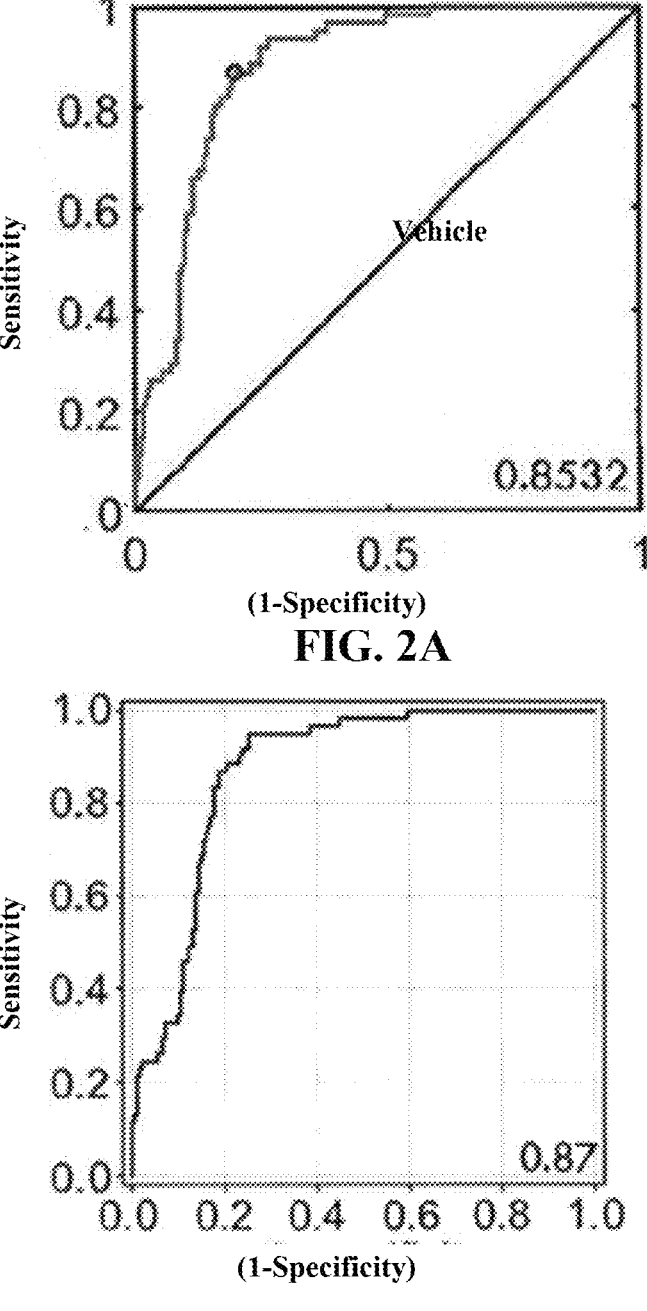
FIG. 2A shows using the array measuring method and interpretation device for ultrasonic detection of middle ear effusion of the present invention to measure and interpret the receiver operating characteristic curve of normal subjects and middle ear effusion condition in patients with middle ear effusion.
FIG. 2B is a receiver operating characteristic curve for measuring and interpreting middle ear effusion in normal subjects and patients with middle ear effusion using only a single probability density function parameter.

The ROC analysis curves of the three experimental groups and the control groups are shown in FIGS. 2-4 respectively; in which FIG. 2A and FIG. 2B show the test results of group (1) whether there is middle ear effusion or not. FIG. 2A is an embodiment of the present invention. After using weighted probability density function parameters to interpret the condition of normal subjects and patients with middle ear effusion, the AUROC obtained by ROC curve analysis is 0.85. FIG. 2B shows the control group, using only a single probability density function parameter to interpret the condition of normal subjects and patients with middle ear effusion. The AUROC obtained by analyzing the ROC curve is 0.87, which is similar to the above mentioned. This result shows that using the measurement and interpretation method and device of the present invention can well determine whether a patient has middle ear effusion.

Figure 3A:
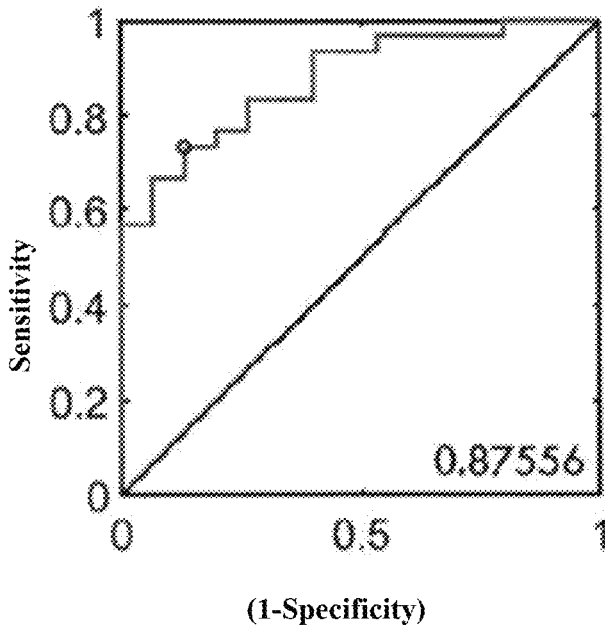
FIG. 3A shows using the array measuring method and interpretation device for ultrasonic detection of middle ear effusion of the present invention to measure and interpret the receiver operating characteristic curve of the condition of middle ear effusion in patients with mild to moderate middle ear effusion and severe middle ear effusion.
Figure 3B:
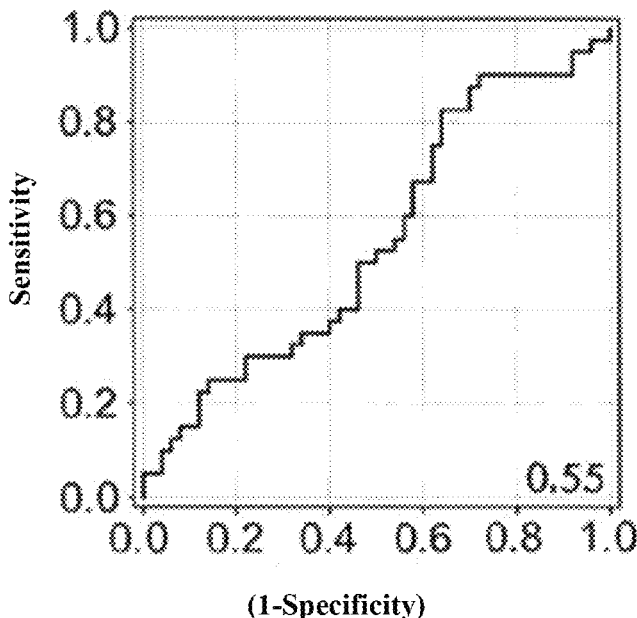
FIG. 3B is a receiver operating characteristic curve for measuring and interpreting the condition of middle ear effusion in patients with mild to moderate middle ear effusion and severe middle ear effusion using only a single probability density function parameter.

FIG. 3A and FIG. 3B show the test results of the severity of middle ear effusion in group (2). FIG. 3A is an embodiment of the present invention, using the measurement and interpretation method and device of the present invention, after using weighted probability density function parameters to interpret the condition of patients with moderate middle ear effusion and severe middle ear effusion, the AUROC obtained by ROC analysis is as high as 0.87. FIG. 3B shows the control group. After using only a single probability density function parameter to interpret the condition of patients with mild to moderate middle ear effusion and severe middle ear effusion, the AUROC obtained by ROC analysis is only 0.53, showing that the measurement and interpretation method does not have the ability to predict the severity of middle ear effusion. The result shows that the measurement and interpretation method and device of the present invention can be used to determine the severity of middle ear effusion in patients.

Figure 4A:
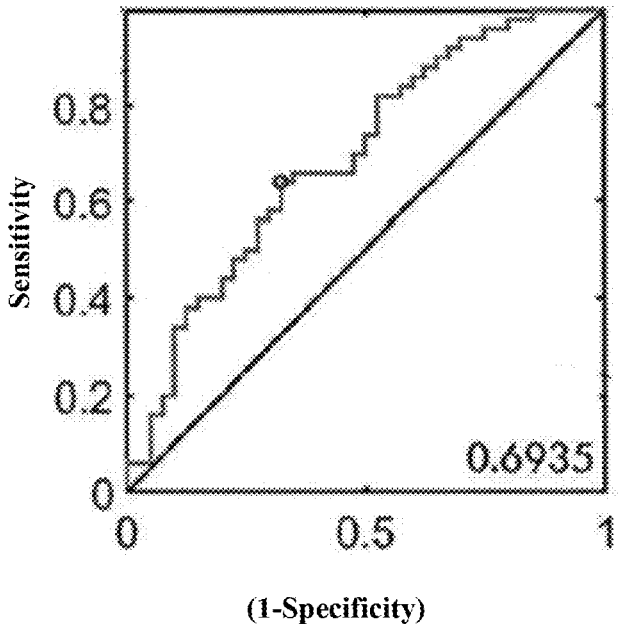
FIG. 4A shows using the array measuring method and interpretation device for ultrasonic detection of middle ear effusion of the present invention to measure and interpret the receiver operating characteristic curve of the condition of middle ear effusion in patients with serous middle ear effusion and mucinous middle ear effusion.
Figure 4B:
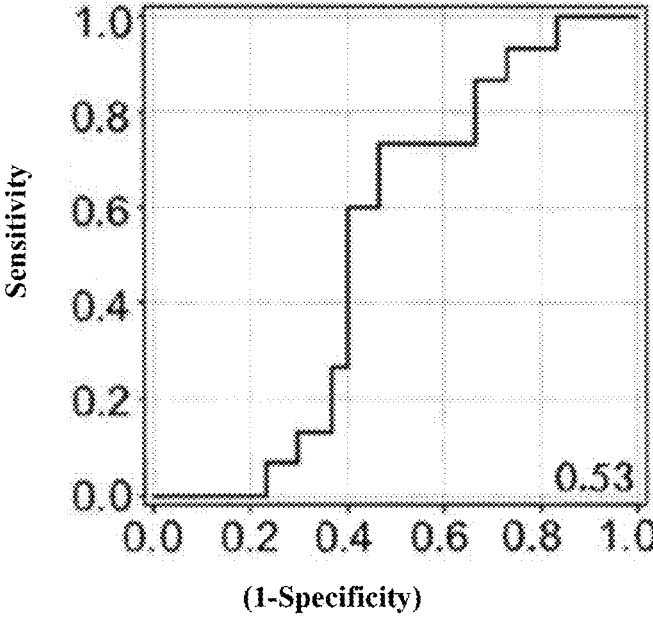
FIG. 4B is a receiver operating characteristic curve for measuring and interpreting the condition of middle ear effusion in patients with serous middle ear effusion and mucinous middle ear effusion using only a single probability density function parameter.

FIG. 4A and FIG. 4B are the test results of the fluid properties of middle ear effusion in group (3). FIG. 4A is an embodiment of the present invention, with the measurement and interpretation method and device of the present invention, after using weighted probability density function parameters to interpret the condition of patients with serous middle ear effusion and mucinous middle ear effusion, the AUROC obtained by analyzing with ROC is effectively improved to 0.69. FIG. 4B shows the control group. After using only a single probability density function parameter to interpret the condition of patients with serous middle ear effusion and mucinous middle ear effusion, the AUROC obtained by ROC analysis is only 0.55, showing that the measurement and interpretation method is nearly impossible to predict the fluid characteristics of middle ear effusion. The result shows that using the measurement and interpretation method and device of the present invention can effectively improve the ability to determine the fluid properties (i.e., serous or mucinous) in patients with middle ear effusion.

Therefore, the array measuring method and interpretation device for ultrasonic detection of middle ear effusion of the present invention uses a single-element ultrasonic probe to use the mastoid surface behind the subject's ear as the sound window and send ultrasonic signals, and then receives and analyzes the ultrasonic echo signal returned according to the condition of middle ear effusion of the subject to perform non-invasive measurements. Since the area at the mastoid is large, and there is no relevant prior art to disclose the detection position that can reflect the best measurement results, if the measurement position cannot be accurately controlled, the results would be inaccurate due to the uncertainty of the measurement position.

Accordingly, in the present invention, in order to optimize the calculation and analysis methods of the overall information and integrate it into the original operating interface, achieving easy operation and rapid classification of the condition and nature of middle ear effusion, improving the accuracy and predictability of ultrasonic-based non-invasive measurement methods and their devices, the subject's mastoid surface is further divided into a plurality of array measurement areas, and the ultrasonic echo signals of each array measurement area are obtained respectively. After calculating a probability density function parameter of each array measurement area, the data analysis software in the analysis unit is combined with linear discriminant analysis based on machine learning for pre-training to find out the importance weight of each separated measurement area in determining the condition of middle ear effusion. After weighting the probability density function parameters of each measurement area, compared with using a single parameter, the obtained new parameters can not only maintain a good ability to determine whether a patient has middle ear effusion, but can also be used to determine the severity of the patient's middle ear effusion. It can also effectively improve the ability to determine the nature (i.e., serous or mucinous) of middle ear effusion in patients.

In summary, the array measuring method and interpretation device for ultrasonic detection of middle ear effusion of the present invention can improve the existing shortcomings of the prior art. It has the advantages of non-invasiveness, no radiation, and can be used anywhere and at any time. It is especially suitable for measuring middle ear effusion in children. And if the present invention is used to repeatedly measure the user's middle ear effusion before and after surgery, it can be used to evaluate whether the middle ear effusion has been cleared before and after surgery. Most importantly, the data analysis method of the present invention can also reduce the uncertainty caused by subjective judgment, making the diagnosis of middle ear effusion faster, more convenient to operate, and the test results more accurate.

What is claimed is:

1. An array measuring and interpretation device for ultrasonic detection of middle ear effusion, comprising:

an ultrasonic probe, configured to be attached to a mastoid surface behind a user's ear and configured to send an ultrasound wave, wherein the mastoid surface comprises a plurality of array measurement areas, and an ultrasonic echo signal is generated in each array measurement area according to the user's condition of the middle ear effusion;

an ultrasonic receiver, connected to the ultrasonic probe and configured to receive the ultrasonic echo signal of each array measurement area;

an analog-to-digital converter, connected to the ultrasonic receiver and configured to convert the ultrasonic echo signal of each array measurement area into a digital signal; and a processor, connected to the analog-to-digital converter, wherein the processor is configured to calculate a probability density function parameter of each array measurement area based on the digital signal, and is configured to use a pre-trained model to determine a calculated weight corresponding to the probability density function parameter of each array measurement area, wherein the processor is configured to multiply the probability density function parameter of each array measurement area with the calculated weight to generate a weighted probability density function parameter in each array measurement area, and each of the weighted probability density function parameters are summed together for quantifying degree of middle ear effusion of the user, thereby determining the user's condition of the middle ear effusion.

2. The array measuring and interpretation device for ultrasonic detection of middle ear effusion according to claim 1, wherein the calculated weight of the probability density function parameter corresponding to each array measurement area is found using linear discriminant analysis and the pre-trained model.

3. The array measuring and interpretation device for ultrasonic detection of middle ear effusion according to claim 1, wherein the array measuring and interpretation device for ultrasonic detection of middle ear effusion improves accuracy of determining severity of middle ear effusion of the user.

4. The array measuring and interpretation device for ultrasonic detection of middle ear effusion according to claim 1, wherein the array measuring and interpretation device for ultrasonic detection of middle ear effusion improves accuracy of determination of types of the user's middle ear effusion.

5. The array measuring and interpretation device for ultrasonic detection of middle ear effusion according to claim 1, wherein the ultrasonic probe is a low frequency delay probe.

6. The array measuring and interpretation device for ultrasonic detection of middle ear effusion according to claim 1, wherein the condition of the middle ear effusion includes various types of otitis media, middle ear effusion, mastoid effusion, mastoiditis, and tracking before and after ear tube implantation.

7. An array measuring and interpretation method for ultrasonic detection of middle ear effusion, comprising the following steps:

attaching an ultrasonic probe to a mastoid surface behind a user's ear and sending an ultrasound wave, wherein the mastoid surface comprises a plurality of array measurement areas, an ultrasonic echo signal is generated in each array measurement area according to the user's condition of the middle ear effusion, and the ultrasonic echo signal of each array measurement area is received by using an ultrasonic receiver;

converting the ultrasonic echo signal of each array measurement area into a digital signal by using an analog-to-digital converter; and calculating a probability density function parameter of each array measurement area via a processor based on the digital signal, and using a pre-trained model to find a calculated weight based on signal characteristics corresponding to the probability density function parameter of each array measurement area, wherein the processor is configured to multiply the probability density function parameter of each array measurement area with the calculated weight to generate a weighted probability density function parameter in each array measurement area, and each of the weighted probability density function parameters are summed together for quantifying degree of middle ear effusion of the user, thereby determining the user's condition of the middle ear effusion.

8. The array measuring and interpretation method for ultrasonic detection of middle ear effusion according to claim 7, wherein the calculated weight of the probability density function parameter corresponding to each array measurement area is found using linear discriminant analysis and the pre-trained model.

9. The array measuring and interpretation method for ultrasonic detection of middle ear effusion according to claim 7, wherein the mastoid surface is divided into array measurement areas.

10. The array measuring and interpretation method for ultrasonic detection of middle ear effusion according to claim 7, wherein the array measuring and interpretation method for ultrasonic detection of middle ear effusion improves accuracy of determining severity of middle ear effusion of the user.

11. The array measuring and interpretation method for ultrasonic detection of middle ear effusion according to claim 7, wherein the array measuring and interpretation method for ultrasonic detection of middle ear effusion improves accuracy of determination of types of the user's middle ear effusion.

* * * * *